United States Patent
Dieringer et al.

(10) Patent No.: US 9,335,188 B2
(45) Date of Patent: May 10, 2016

(54) PRESSURE MANAGEMENT SYSTEM FOR SENSORS

(71) Applicant: General Electric Company, Schenectady, NY (US)

(72) Inventors: Jon Albert Dieringer, Schenectady, NY (US); Roger Neal Johnson, Hagaman, NY (US); Cheryl Margaret Surman, Albany, NY (US)

(73) Assignee: General Electric Company, Niskayuna, NY (US)

(*) Notice: Subject to any disclaimer, the term of this patent is extended or adjusted under 35 U.S.C. 154(b) by 319 days.

(21) Appl. No.: 13/931,319

(22) Filed: Jun. 28, 2013

(65) Prior Publication Data
US 2015/0000385 A1  Jan. 1, 2015

(51) Int. Cl.
| | | |
|---|---|---|
| *G01D 11/24* | (2006.01) | |
| *G01N 1/16* | (2006.01) | |
| *G01N 1/20* | (2006.01) | |
| *G01N 33/28* | (2006.01) | |
| *G01N 27/02* | (2006.01) | |

(52) U.S. Cl.
CPC ............... *G01D 11/245* (2013.01); *G01N 1/16* (2013.01); *G01N 1/2035* (2013.01); *G01N 33/2823* (2013.01); *G01N 27/023* (2013.01)

(58) Field of Classification Search
CPC ... G01N 1/16; G01N 1/2035; G01N 33/2823; G01N 2001/1445; G01D 11/245
See application file for complete search history.

(56) References Cited

U.S. PATENT DOCUMENTS

| | | | | |
|---|---|---|---|---|
| 2,440,617 | A * | 4/1948 | Seebold | C10G 33/04 |
| | | | | 516/136 |
| 3,301,063 | A * | 1/1967 | Kisling, III | E21B 47/06 |
| | | | | 73/152.53 |
| 3,651,697 | A * | 3/1972 | Ianuzzi | G01C 5/06 |
| | | | | 73/300 |
| 4,199,991 | A | 4/1980 | Kodama | |
| 4,244,229 | A | 1/1981 | Pullen | |
| 5,119,066 | A | 6/1992 | Ballyns | |
| 5,280,141 | A | 1/1994 | Neeleman et al. | |
| 5,524,492 | A | 6/1996 | Frick et al. | |
| 5,563,347 | A | 10/1996 | Martin et al. | |
| 6,206,133 | B1 * | 3/2001 | Paulsson | E21B 17/1035 |
| | | | | 166/206 |
| 6,311,561 | B1 | 11/2001 | Bang et al. | |
| 6,551,853 | B2 | 4/2003 | Toyoda | |
| 6,889,565 | B2 | 5/2005 | Deconde et al. | |
| 7,095,064 | B2 | 8/2006 | Hamamoto | |
| 7,258,017 | B1 | 8/2007 | Hedtke | |
| 7,434,469 | B2 | 10/2008 | Hedtke | |
| 8,043,858 | B2 * | 10/2011 | McDaniel | C10G 31/08 |
| | | | | 208/188 |
| 8,061,050 | B2 | 11/2011 | Argov | |
| 2010/0015720 | A1 * | 1/2010 | McDaniel | C10G 31/08 |
| | | | | 436/164 |

\* cited by examiner

*Primary Examiner* — Peter Macchiarolo
*Assistant Examiner* — Nathaniel Kolb
(74) *Attorney, Agent, or Firm* — John P. Darling

(57) ABSTRACT

A pressure management system for sensors is provided. The system includes a sampling assembly. The sampling assembly is configured to hold a first portion of a test fluid. Further, the system includes at least one sensor disposed proximate to the sampling assembly. The sensor is configured to determine at least one property of the test fluid. The system also includes a housing that is disposed around the sampling assembly. The housing defines a fluid chamber that houses a balancing fluid. Furthermore, the system includes a flexible device disposed in the fluid chamber that draws a second portion of the test fluid. The flexible device is configured to balance pressure exerted by the test fluid on the sampling assembly by exerting pressure on the balancing fluid with the second portion of the test fluid.

19 Claims, 4 Drawing Sheets

PRESSURE MANAGEMENT SYSTEM FOR SENSORS

BACKGROUND

The present invention relates generally to sensors, and more particularly, to a system for management of pressure being exerted on sensors in harsh environments.

Wells are being used currently to utilize resources available under the surface of the earth. Natural resources such as oils, minerals, and gases are obtained through these wells with the help of pumps and valve configurations. The pressure present in the wells enables natural resources to be pulled up to the surface of the earth from where the natural resources are transported to refineries or storage containers. Pump and valve configurations are also utilized in other systems such as desalination plants, wastewater management systems and the like. Since the equipment required to produce output from these systems are located deep under the surface of the earth, it becomes difficult to check their condition periodically. Sensors are placed alongside such equipment to monitor their health and provide well managers with adequate time to fix ill-functioning equipment.

Sensing systems are also deployed in systems such as separators, desalters, wastewater management systems, and oil quality control systems to analyze compositions of the fluid being extracted from under the surface of the earth. Further, flow meters are also installed in wells to analyze the flow dynamics of available resources. Chemicals are also injected into the wells to protect them from corrosion, and ill-effects caused by foam and other such materials. Injection of chemicals in wells is generally carried through chemical-injection management systems that are controlled using flow meters.

It has been observed that operating efficiency of sensing systems, such as flow meters, and solenoid-coil based sensors deteriorates with increase in operating temperature and pressure. Temperature effect on sensing systems is compensated with the use of insulation material in the sensing system vicinity.

However, for pressure compensation the use of isolation layers does not yield the same results. It has been observed that the response from sensing systems is affected in the presence of metallic absorption shields. To avoid the metallic shield to interfere with the response from sensing systems, sensing systems are wrapped in radio-frequency (RF) absorbing materials and shielded. However, RF absorbing materials that can be utilized in deep environments where the operating frequency is less than 10 MHz are not easily available.

Hence, there is a need for a system that compensates for pressure exerted on sensing systems deployed in harsh environments.

BRIEF DESCRIPTION

In one embodiment, a system including a sampling assembly is provided. The sampling assembly is configured to hold a first portion of a test fluid. Further, the system includes at least one sensor disposed proximate to the sampling assembly. The sensor is configured to determine at least one property of the test fluid. The system also includes a housing that is disposed around the sampling assembly. The housing defines a fluid chamber that houses a balancing fluid. Furthermore, the system includes a flexible device disposed in the fluid chamber that draws a second portion of the test fluid from the first portion of the test fluid. The flexible device is configured to balance pressure exerted by the test fluid on the sampling assembly by exerting pressure on the balancing fluid with the second portion of the test fluid.

In another embodiment, a system including a vessel system is provided. The vessel system is configured to hold a test fluid. The system further includes a sampling assembly that is coupled with the vessel system. The sampling assembly is configured to draw a first portion of the test fluid from the vessel system. The system also includes at least one sensor that is disposed proximate to the sampling assembly. The sensor is configured to determine at least one property of the test fluid. Furthermore, the system includes a pressure balancing device configured to protect the at least one sensor from pressure change. The pressure balancing device includes a housing and a flexible device. The housing is disposed around the sampling assembly and is configured to define a fluid chamber that houses a balancing fluid. The flexible device is disposed in the fluid chamber and is configured to draw a second portion of the test fluid from the first portion. The flexible device is configured to balance pressure exerted by the test fluid on the sampling assembly by exerting pressure on the balancing fluid with the second portion of the test fluid.

DRAWINGS

Other features and advantages of the present disclosure will be apparent from the following more detailed description of the preferred embodiment, taken in conjunction with the accompanying drawings which illustrate, by way of example, the principles of certain aspects of the disclosure.

DETAILED DESCRIPTION

Figure 1:
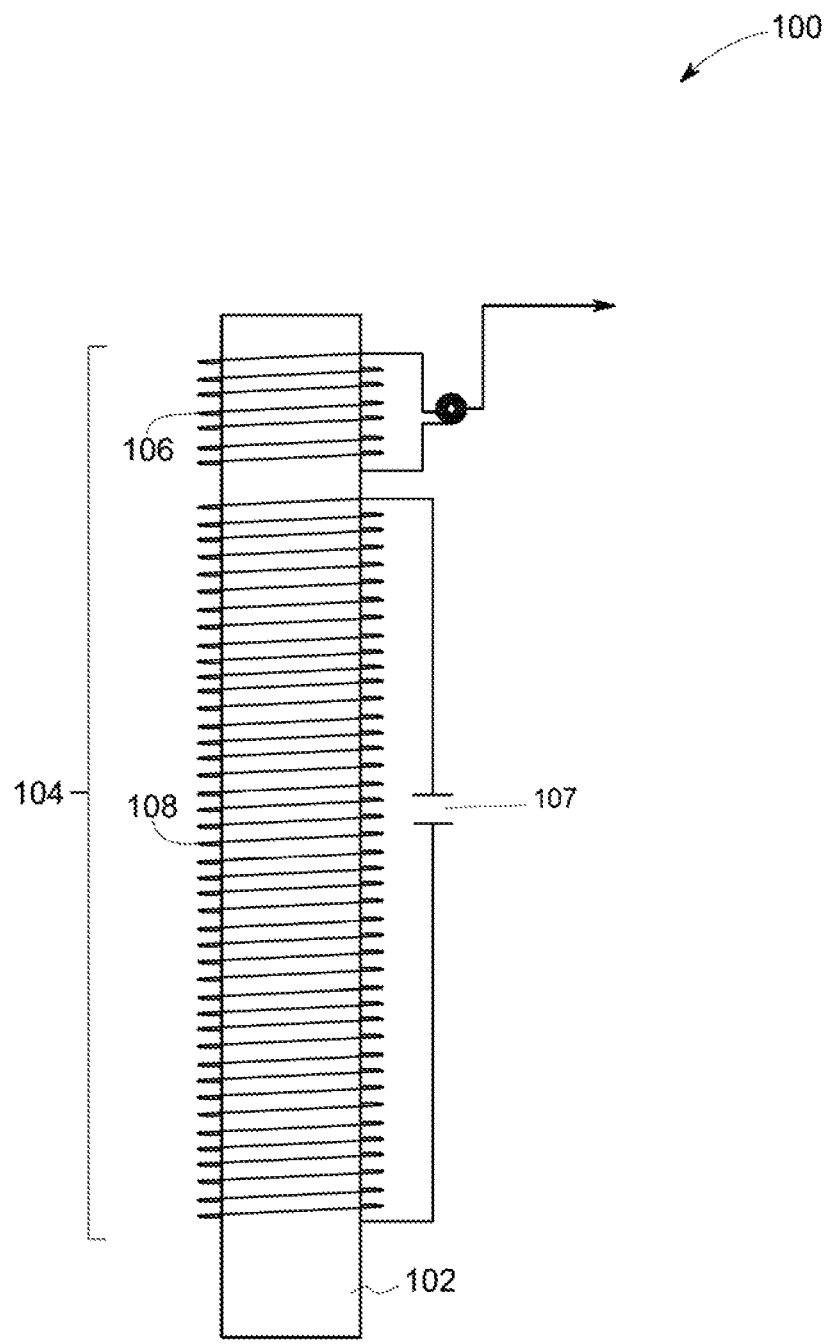
FIG. 1 illustrates a schematic view of a typical sensing system deployed to measure at least one property of the test fluid.

Reference will be made below in detail to exemplary embodiments of the invention, examples of which are illustrated in the accompanying drawings. Wherever possible, the same reference numerals used throughout the drawings refer to the same or like parts.

Sensing systems are utilized in wells that are dug to recover natural resources from under the surface of the earth. Sensing systems are utilized to sense a plurality of properties pertaining to equipment installed to recover the natural resources. Sensing systems are also installed to analyze the resources being recovered from the well. Sensing systems determine a plurality of properties pertaining to the resources. The properties being determined by the sensing systems include, but are not limited to, temperature, composition of the emulsion, level of a particular component in the composition and the like. Similarly, sensing systems are utilized to analyze fluids being utilized in systems such as waste water management systems, or desalination systems. To utilize the sensing systems excitation signals are provided to the sensing systems. A response of the sensing systems to the interaction between the excitation signal and the fluid is captured to determine one of the plurality of properties. To allow for the excitation signal to interact with the fluid, the fluid is drawn from storage vessels and stored in sampling assemblies. Examples of storage vessels include, but are not limited to desalters, biochemical reactors, containers, and others known in the art. Samples of the fluid are drawn from the vessels with the help of sampling assemblies such as try-line assembly, or a swing arm assembly, or a dipstick. The sensing systems are placed proximate to the sampling assemblies to generate the response required for analysis and determination. In certain cases, the sensing systems include solenoid coil based sensors. The solenoid coil based sensors are wound around the sampling assembly. One coil from the sensing system is provided with the excitation signal and the response is collected from another coil. The pressure exerted by the environment on the sensing system, when the sensing system is disposed with the sampling assembly, can cause the sensing system to malfunction. A pressure management system, as will be described in greater detail in forthcoming paragraphs, provides for balancing the pressure being exerted on the sensing system. The pressure management system includes a housing. The housing, typically, is of cylindrical shape and may be defined by a sheet of metallic material. The housing defines a fluid chamber in which balancing fluid is disposed. The sampling assembly, that holds test fluid from the vessel, is enclosed within the housing. A flexible device is disposed in the fluid chamber to be proximate to the sampling assembly. The housing is sealed from both sides with end caps. One of the end caps includes a plurality of apertures to couple exit ports of the vessels with input ports of the sampling assembly and also provide for input ports to the housing to allow for balancing fluid to enter the fluid chamber. The volume of the housing is filled with the balancing fluid. During operation, the test fluid is simultaneously made to enter the sampling assembly and the flexible device. The test fluid enters both, the flexible device and the sampling assembly, through a connecting device such as a tee-connector. When the test fluid enters the flexible device, the flexible device expands and the pressure exerted by the entering test fluid is distributed to the walls of the housing through the balancing fluid. The sampling assembly thus sees a simple flow channel of the test fluid without experiencing the high pressures at which the test fluid enters the housing. The system for pressure management is explained in greater detail in the following paragraphs.

FIG. 1 illustrates a schematic view of a typical sensing system deployed to measure at least one property of the test fluid. The sensing system 100 typically includes a sampling assembly 102, and a sensor assembly 104. The sampling assembly 102, as shown in FIG. 1, receives test fluid from vessels that are configured to store and process fluid extracted from under the surface of the earth. Nonlimiting examples of vessels include reactors, chemical reactors, biological reactors, storage vessels, containers, and others known in the art. The fluid present in the vessel may, for example, be a mixture of oil, water, and a demulsifier. A portion of the fluid is obtained from the vessel and stored in the sampling assembly 102 as the test fluid. The test fluid is drawn from the vessel using multiple configurations such as try-line assembly, dipstick assembly, or a swing-arm assembly. The sampling assembly 102 may be at least one output conduit of these configurations that are used to draw the test fluid from the vessel. Exemplary embodiments of vessels with configurations to draw the test fluid are explained in greater detail in FIGS. 2 and 3.

According to certain embodiments, the sampling assembly is a baffle tube. The sampling assembly 102 may be made of material that is resistant to fouling such as Polytetrafluoroethylene (PTFE), a synthetic fluoropolymer of tetrafluoroethylene. The sensor assembly 104 is placed proximate to the sampling assembly 102 such that walls of the sampling assembly 102 separate the sensor assembly 104 from the test fluid present in the sampling assembly 102.

The sensor assembly 104 may be designed to determine at least one of a plurality of properties associated with the test fluid. The plurality of properties include, but are not limited to, temperature, pressure, composition, level of a particular component in the composition and the like. According to one embodiment, the sensor assembly 104 configured to determine a composition of the test fluid includes a solenoid-coil based assembly. The sensor assembly 104, as illustrated in FIG. 1, is a coil-based sensor.

The sensor assembly 104, as illustrated in FIG. 1, includes a primary coil 106, and at least one secondary coil 108. The primary coil 106 and the secondary coil 108, according to certain embodiments, are wound around a holding area of the sampling assembly 102. The sampling assembly 102 acts as a layer of dielectric material between the test fluid and the sensing assembly 104. The layer of dielectric material plays an important role in creating a response at the secondary coil 108.

The primary coil 106 and the secondary coil 108 are made from metallic wires. According to certain embodiments, number of turns of the primary and secondary coils are selected based on a desired range of response that the sensor assembly 104 is expected to cover. The primary and secondary coils 106 and 108 are made from metallic material such as copper, and aluminum. The primary coil 106 and the secondary coil 108, according to one embodiment, are disposed proximate to each other. In the illustrated embodiment, the primary coil 106 encapsulates the secondary coil 108.

The primary coil 106 and the secondary coil 108 are further coupled with a capacitive element 107 to create an inductive capacitive resonant circuit from the primary and secondary coil 106 and 108. The primary coil 106 is further coupled with a power source that provides excitation signals. The secondary coil 108, according to certain embodiments, is coupled with an analyzer. The secondary coil 108 and the analyzer may be coupled through wired or wireless communication channels. The analyzer, according to certain embodiments, is an impedance analyzer. According to certain embodiments, the analyzer is at least one of dual channel vector voltmeter, or a vector network analyzer. The analyzer is configured to measure responses induced in the secondary coil 108 when excitation signal is provided to the primary coil 106. The properties determined by the analyzer include, among others, changes in capacitance, inductance, and resistance of the secondary coil 108, and the resonant frequency of the secondary coil 108. The properties measured by the analyzer are communicated to a processing sub-system through wired or wireless communication channels. The processing sub-system is configured to determine a relationship between the parameters determined by the analyzer and one of a plurality of properties associated with the test fluid present in the sampling assembly 102.

According to certain embodiments, the sensor assembly 104 includes more than one secondary coil 108. Multiple secondary coils are coupled to the primary coil 106. Each secondary coil is configured to respond to different components present in the test fluid present in the sampling assembly 102.

Figure 2:
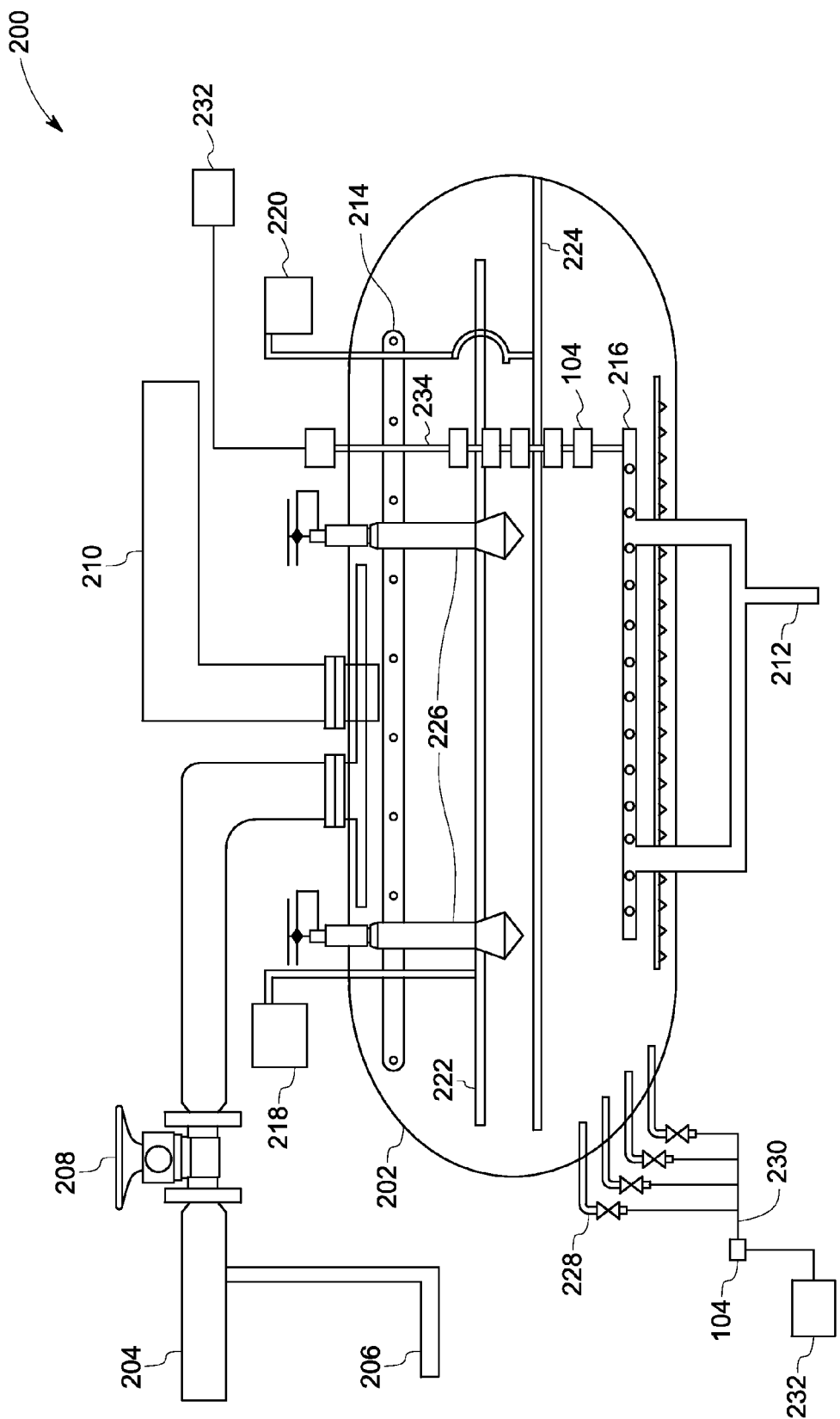
FIG. 2 is a schematic diagram of an embodiment of a desalter.

FIG. 2 is a schematic diagram of an embodiment of a desalter. The sensor assembly 104, as illustrated in FIG. 1 is disposed in the desalter to determine at least one property of the fluid stored in the desalter. The desalter 200 is an embodiment of a vessel in which embodiments of the present technique may be disposed. The desalter 200 includes a desalter vessel 202. Fluid such as raw oil enters the desalter 200 through input 204 and is mixed with water from water input 206. The combination of the fluid and water flows through mixing valve 208 and into the desalter vessel 202. The desalter 200 includes a treated oil output 210 and a wastewater output 212. Disposed within the desalter vessel 202 are an oil collection header 214 and a water collection header 216. Transformer 218 and transformer 220 provide electricity to top electrical grid 222 and bottom electrical grid 224. Disposed between top electrical grid 222 and bottom electrical grid 224 are emulsion distributors 226.

In operation, crude oil mixed with water enters the desalter vessel 202 and the two fluids are mixed and distributed by emulsion distributors 226 thereby forming an emulsion. The emulsion is maintained between the top electrical grid 222 and the bottom electrical grid 224. Salt containing water is separated from the oil/water mixture by the passage through the top electrical grid 222 and bottom electrical grid 224 and drops towards the bottom of the desalter vessel 202 where it is collected as waste water from the wastewater output 212.

Control of the level of the emulsion layer and characterization of the contents of the oil-in-water and water-in-oil emulsions is important in the operation of the desalter 200. Determination of the level of the emulsion layer may be accomplished by placing the sensor assembly proximate to a sampling assembly such as a try-line assembly 228 coupled to the desalter vessel 202. The sensor assembly 104 is disposed on at least one try-line output conduit 230. The sensor assembly 104 may be coupled to a data collection component 232. In operation, the sensor assembly 104 may be used to measure the level of water and the oil and to enable operators to control the process. The try-line assembly 228 may be a plurality of pipes open at one end inside the desalter vessel 202 with an open end permanently positioned at the desired vertical position or level in the desalter vessel 202 for withdrawing portions of the fluid in the vessel 202 such that test fluid is obtained. There are generally a plurality of sample pipes in a processing vessel, each with its own sample valve, with the open end of each pipe at a different vertical position inside the unit, so that test fluid can be withdrawn from a plurality of fixed vertical positions in the unit. Another approach to drawing portions of the fluid in the vessel 202 is to use a swing arm sampler. A swing arm sampler is a pipe with an open end inside the desalter vessel 202 typically connected to a sampling valve outside the unit. It includes an assembly used to change the vertical position of the open end of the angled pipe in the desalter 200, by rotating it, so that test fluid can be withdrawn (or sampled) from any desired vertical position.

Another method to measure the properties of the fluid in the vessel is to dispose at least one sensor assembly 104 on a dipstick 234. The dipstick 234 may be a rod with a sensor assembly 104 that is inserted into the desalter vessel 202. Measurements are made at a number of levels. Alternately, the dipstick 234 may be a stationary rod having a plurality of multiplexed sensor assemblies 104. The sensor assembly 104 may be coupled to a data collection component 232 that collects data from the various readings for further processing.

Figure 3:
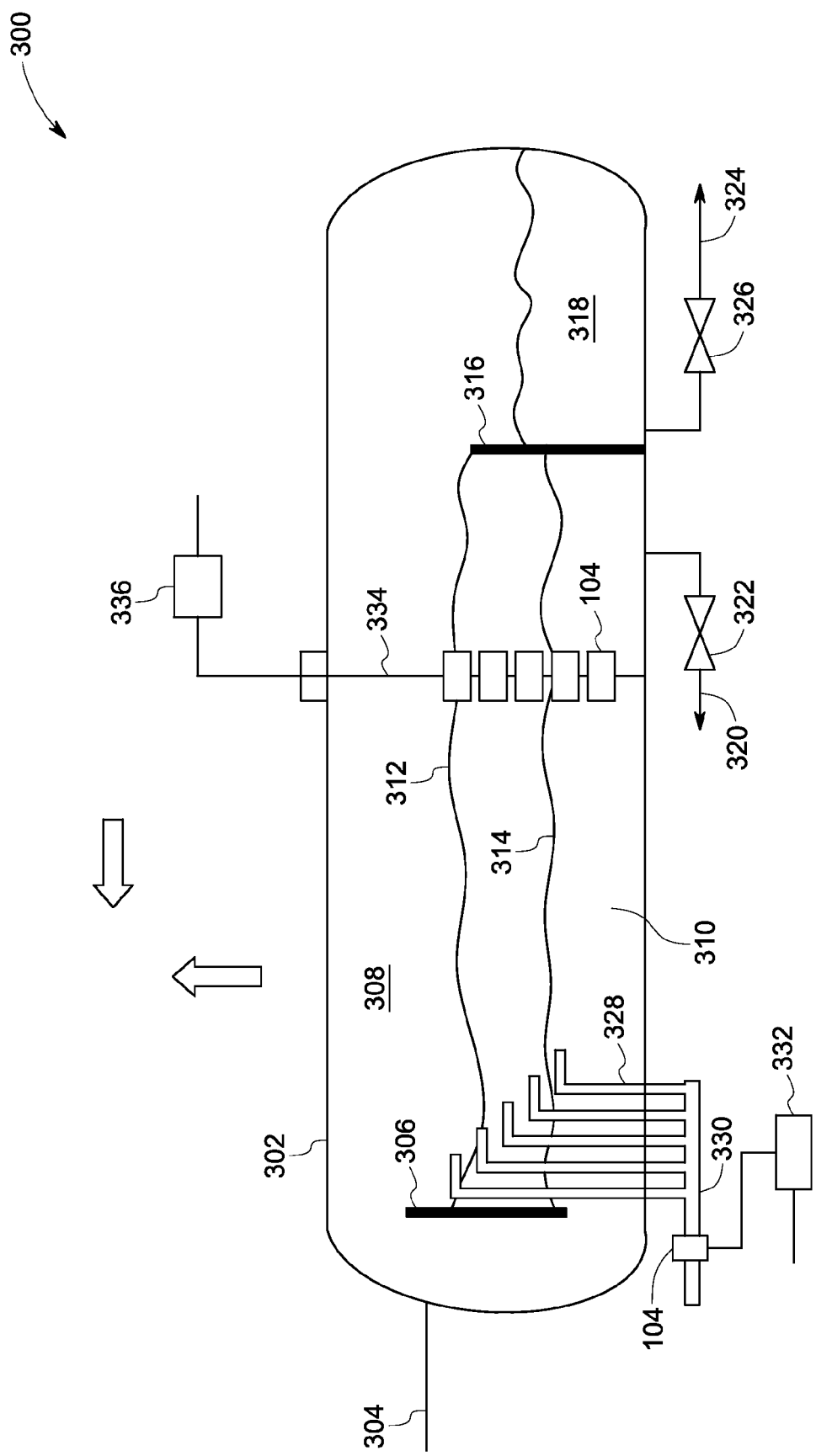
FIG. 3 is a schematic diagram of an embodiment of a separator.

Another embodiment of a fluid processing system where the sensor assembly 104 may be disposed is a separator 300 illustrated in FIG. 3. The separator 300 includes a separator vessel 302 having an input conduit 304. Fluid such as crude oil flowing from input conduit 304 impacts an inlet diverter 306. The impact of the crude oil on the inlet diverter 306 causes water particles to begin to separate from the crude oil. The crude oil flows into the processing chamber 308 where it is separated into a water layer 310 and an oil layer 312. The crude oil is conveyed into the processing chamber 308 below the oil/water interface 314. This forces the inlet mixture of oil and water to mix with the water continuous phase in the bottom of the vessel and rise through the oil/water interface 314 thereby promoting the precipitation of water droplets which are entrained in the oil. Water settles to the bottom while the oil rises to the top. The oil is skimmed over a weir 316 where it is collected in oil chamber 318. Water may be withdrawn from the system through a water output conduit 320 that is controlled by a water level control valve 322. Similarly oil may be withdrawn from the system through an oil output conduit 324 controlled by an oil level control valve 326. The height of the oil/water interface may be detected using a try-line assembly 328 having at least one sensor assembly 104 disposed in a try-line output conduit 330 and coupled to a data processor 332. Alternately a dip stick 334 having at least one sensor assembly 104 coupled to a processor 336 may be used to determine the level of the oil/water interface 314. The determined level is used to control the water level control valve 322 to allow water to be withdrawn so that the oil/water interface is maintained at the desired height.

When the sensor assembly 104 is disposed on the try-line assembly, or the swing-arm assembly, or the dipstick as illustrated in FIGS. 2 and 3, the pressure exerted by the fluid present in the vessels such as the separator vessel and the desalter vessel may cause damage to the sensor assembly 104. The try-line output conduit, the swing-arm sampler, or the dipstick may be disposed within the pressure management system, as illustrated in FIG. 4, to protect the sensor assembly 104 from damages caused by the fluid pressure.

Figure 4:
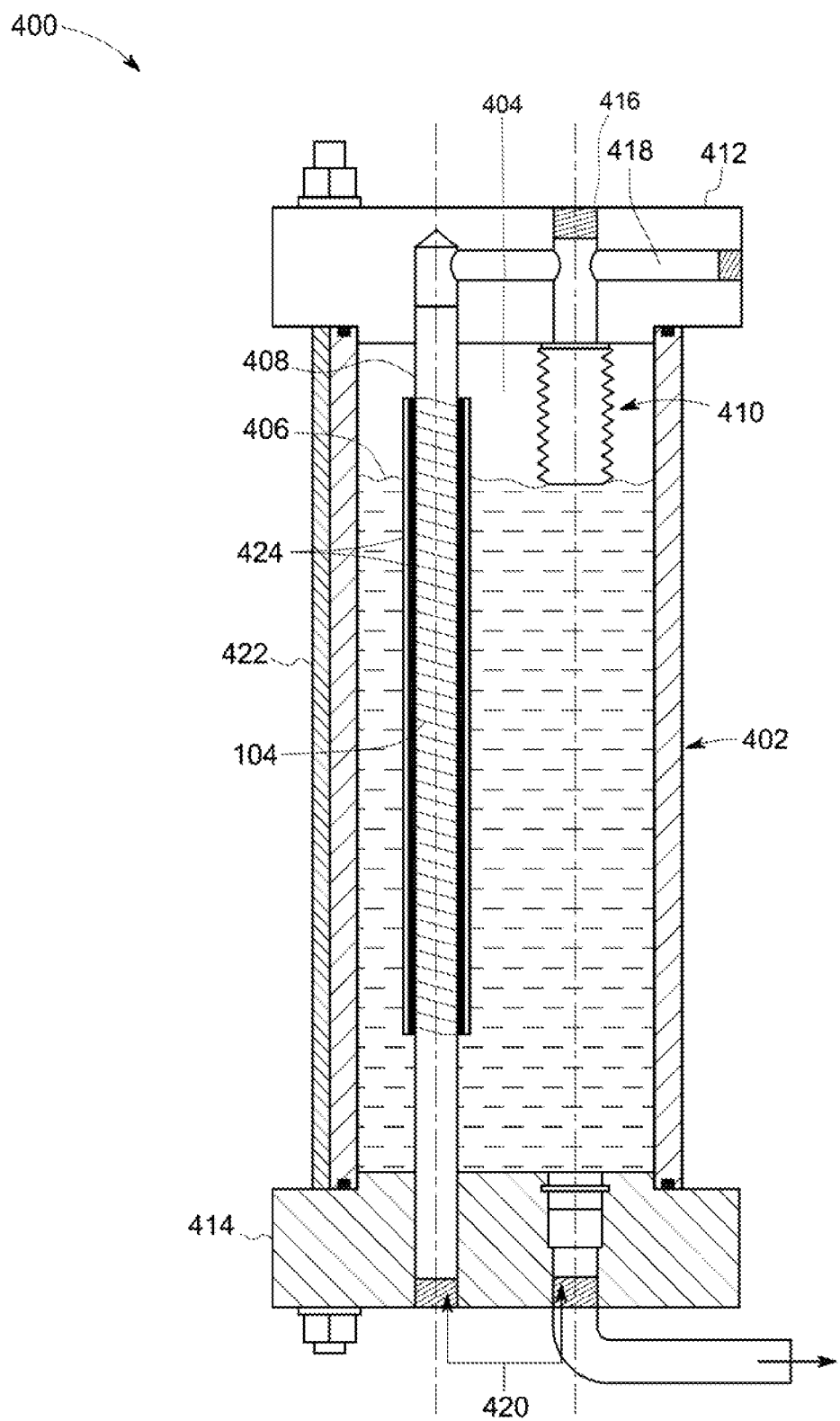
FIG. 4 illustrates a pressure management system for a sensing system to be disposed in fluid vessels.

FIG. 4 illustrates a pressure management system 400 for a sensor assembly 104 to be disposed in fluid vessels such as desalters, and fluid separation vessels. The pressure management system 400 includes a housing 402. The housing 402, typically, is of cylindrical shape. In one embodiment, one end of a sheet made from metal is joined to another end of the sheet to define a hollow cylindrical structure. The hollow cylindrical structure may be utilized as the housing 402. The hollow portion of the housing 402 defines a fluid chamber 404. The fluid chamber 404 is configured to house a balancing fluid 406. Sampling assembly 408, on which the sensor assembly 104 is disposed is enclosed within the housing 402. A flexible device 410 is also disposed within the housing 402. The sampling assembly 408 may be a tube configured to hold a test fluid. The test fluid may be a portion of fluid stored in the fluid vessels. For example, the test fluid may be an oil-water emulsion stored in a desalter as illustrated in FIG. 3. The sampling assembly 408 may be, in other embodiments, an output conduit of sampling assembly configurations such as the try-line assembly, or the swing arm sampler as illustrated in FIGS. 2 and 3. In some other embodiments, the sampling assembly 408 may be a dipstick, such as dipstick 234, which is configured to be placed in the fluid. The sampling assembly 408 is configured to hold a first portion of the test fluid. In some embodiments, the sampling assembly 408 is surrounded by protective material 424 such as thermal insulation material, or shock absorption material.

The flexible device 410 is configured to expand and contract on application of pressure. The flexible device 410 is configured such that it is sealed from all sides except one, thus allowing for an enclosed space to be defined. The flexible device 410, according to certain embodiments, includes a diaphragm that includes flexible material. According to certain other embodiments, the flexible device 410 is a bellow made from metallic material.

The pressure management system 400 further includes at least one end cap. In the illustrated embodiment, the pressure management system 400 includes end caps 412 and 414. The end caps 412 and 414 are placed on the open ends of the housing 402 such that the housing 402 is sealed from all ends. Further, the sampling assembly 408 and the flexible device 410 are coupled with at least one of the end caps 412 and 414. In the illustrated embodiment, the sampling assembly 408 and the flexible device 410 are sealed with the end cap 412. The end cap 412 includes a plurality of apertures 416. The apertures 416 are configured to couple the sampling assembly 408 with the fluid vessel. For example, the sampling assembly 408 may be coupled with at least one of the try-line output conduits 230. The test fluid drawn from the fluid vessel is configured to enter the sampling assembly 408 through the apertures 416 coupled with the sampling assembly 408. The open end of the flexible device 410 is also coupled with one of the apertures 416 in the end cap 412. According to certain embodiments, O-ring seals are fitted on those ends of the housing 402 that are coupled with the end caps 412 and 414.

The end cap 412 further includes a connecting device 418. According to certain embodiments, the end cap 412 may be manufactured to have a built-in connecting device 418. In other embodiments, the connecting device 418 may be retrofitted into the end cap 412. The connecting device 418 is coupled with an input port of the fluid vessel on one side, and the apertures 416 that are coupled with the sampling assembly 408 and the flexible device 410 on the other side. The connecting device 418 is configured to divert the first portion of the test fluid to the sampling assembly 408 and a second portion of the test fluid into the flexible device 410. In the illustrated embodiment, the connecting device 418 is a tee-connector.

The end cap 414 also includes a plurality of apertures 420 that are configured to couple the sensor assembly 104 with external power source and processing systems. One of the apertures 420 is also configured to drain the fluid chamber 404 in the housing 402. The sampling assembly 408 is fixed to the end cap 414 and is coupled with one of the plurality of apertures 420 to allow for the first portion of the test fluid to leave the sampling assembly 408.

The end caps 412 and 414 are coupled with each other through a plurality of rods 422 that are placed along the length of the housing 402. In some embodiments, a protective layer may be disposed between the plurality of rods 422 to reduce the impact of pressure changes on the housing 402.

During operation, when the fluid from the fluid vessel enters the connecting device 418, a first portion of the test fluid enters the sampling assembly 408 and a second portion of the test fluid simultaneously enters the flexible device 410. The second portion of the test fluid that enters the flexible device 410 causes the flexible device 410 to expand thereby exerting pressure on the balancing fluid 406. The differential pressure created by the entering test fluid in the sampling assembly 408 is thus distributed across the walls of the housing 402. The sampling assembly 408 thus experiences a simple flow of the first portion of the test fluid while the pressure being exerted by the test fluid is distributed to the walls of the housing 402.

In case of a sensor assembly 104 failure or any other operational problems with the pressure management system 400, the balancing fluid 406 is withdrawn from one of the plurality of apertures 420 present in the end cap 414.

The balancing fluid 406 is a fluid selected based on the test fluid entering the sampling assembly 408. In one embodiment, the balancing fluid 406 is a mineral oil based fluid. The balancing fluid 406 is selected such that the balancing fluid 406 does not interrupt with the operations of the sensor assembly 104.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of ordinary skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," etc. are used merely as labels, and are not intended to impose numerical or positional requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose several embodiments of the invention, including the best mode, and also to enable any person of ordinary skill in the art to practice the embodiments of invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described system for management of pressure exerted on sensors, without departing from the spirit and scope of the invention herein involved, it is intended that all of the subject matter of the above description or shown in the accompanying drawings shall be interpreted merely as examples illustrating the inventive concept herein and shall not be construed as limiting the invention.

What is claimed is:

1. A system comprising:
   a sampling assembly configured to hold a first portion of a test fluid;
   at least one sensor disposed proximate to the sampling assembly, wherein the at least one sensor is configured to determine at least one property of the test fluid;
   a housing disposed around the sampling assembly and configured to define a fluid chamber that houses a balancing fluid; and a flexible device disposed in the fluid chamber configured to hold a second portion of the test fluid, wherein the flexible device and the sampling device are simultaneously filled with portions of the test fluid, and wherein the flexible device is configured to balance pressure exerted by the test fluid on the sampling assembly by exerting pressure on the balancing fluid with the second portion of the test fluid wherein the sampling assembly comprises a tube made of dielectric material and the sensor comprises a primary coil capacitively coupled to a secondary coil, wherein the primary coil and the secondary coil are wound around the tube.

2. The system as recited in claim, 1 further comprising a first end cap and a second end cap disposed on open ends of the housing, wherein the first and second end caps seal the open ends of the housing.

3. The system as recited in claim 2, wherein the first end cap comprises an aperture and a connector configured to couple aperture to the sampling assembly and the flexible device, the connector being configured to direct the first portion of the test fluid to the sampling assembly and the second portion of the test fluid to the flexible device.

4. The system as recited in claim 3, wherein the connector is a tee connector.

5. The system as recited in claim 2, further comprising a first aperture in the second end cap configured to drain the first portion of the test fluid from the sampling assembly.

6. The system as recited in claim 1, wherein the flexible device comprises a diaphragm.

7. The system as recited in claim 1, wherein the flexible device comprises a bellow.

8. The system as recited in claim 1, further comprising a protection layer disposed around the sampling assembly.

9. The system as recited in claim 1, wherein the balancing fluid comprises mineral oil.

10. The system as recited in claim 1, wherein the dielectric material is polytetrafluoroethylene.

11. The system as recited in claim 1, further comprising:
an analyzer coupled to the secondary coil and configured to measure responses induced in the secondary coil when an excitation signal is provided to the primary coil; and
a processor configured to determine a relationship between the responses measured by the analyzer and at least one of a plurality of properties associated with the test fluid.

12. The system as recited in claim 11, wherein the analyzer is an impedance analyzer, a dual-channel vector voltmeter, or a vector network analyzer.

13. The system as recited in claim 11, wherein the analyzer measures changes in capacitance, inductance, resistance, and resonant frequency of the secondary coil.

14. The system as recited in claim 11, wherein the processor is configured to determine at least one of a temperature of, a pressure of, a composition of, or a level of a component in the test fluid.

15. A fluid processing system, comprising:
a vessel for containing a mixture of crude oil and water;
the system of claim 1 in fluid communication with the vessel, wherein the test fluid comprises the mixture of crude oil and water.

16. The fluid processing system as recited in claim 15, wherein the mixture of crude oil and water is provided to the sampling assembly by a conduit that removes the mixture of crude oil and water from the vessel.

17. The fluid processing system as recited in claim 15, wherein the sampling assembly is provided within the vessel.

18. A pressure management system for a sensor, comprising:
a sampling assembly configured to hold a first portion of a test fluid, the sampling assembly comprising a tube made of dielectric material;
at least one sensor disposed proximate to the sampling assembly, the sensor comprising a primary coil capacitively coupled to a secondary coil, wherein the primary coil and the secondary coil are wound around the tube, wherein the at least one sensor is configured to determine at least one property of the test fluid;
a housing disposed around the sampling assembly and configured to define a fluid chamber that houses a balancing fluid;
a flexible device disposed in the fluid chamber configured to hold a second portion of the test fluid, wherein the flexible device and the sampling device are simultaneously filled with portions of the test fluid, and wherein the flexible device is configured to balance pressure exerted by the test fluid on the sampling assembly by exerting pressure on the balancing fluid with the second portion of the test fluid;
a first end cap and a second end cap disposed on open ends of the housing, wherein the first and second end caps seal the open ends of the housing, wherein the first end cap comprises an aperture and a connector configured to couple aperture to the sampling assembly and the flexible device, the connector being configured to direct the first portion of the test fluid to the sampling assembly and the second portion of the test fluid to the flexible device;
an analyzer coupled to the secondary coil and configured to measure responses induced in the secondary coil when an excitation signal is provided to the primary coil; and
a processor configured to determine a relationship between the responses measured by the analyzer and at least one of a plurality of properties associated with the test fluid.

19. The pressure management system of claim 18, wherein the analyzer is an impedance analyzer, a dual-channel vector voltmeter, or a vector network analyzer and configured to measures changes in capacitance, inductance, resistance, and resonant frequency of the secondary coil and the processor is configured to determine at least one of a temperature of, a pressure of, a composition of, or a level of a component in the test fluid.

* * * * *